(12) United States Patent
Currell et al.

(10) Patent No.: US 9,044,601 B2
(45) Date of Patent: Jun. 2, 2015

(54) SYSTEM AND METHODS FOR ACCELERATING SIMULATION OF RADIATION TREATMENT

(75) Inventors: Fred Currell, Belfast (GB); Marcus Mendenhall, Nashville, TN (US)

(73) Assignees: Dr. Fred J. Currell, Belfast (IE); Marcus Mendenhall, Nashville, TN (US)

( * ) Notice: Subject to any disclaimer, the term of this patent is extended or adjusted under 35 U.S.C. 154(b) by 281 days.

(21) Appl. No.: 13/125,132

(22) PCT Filed: Oct. 19, 2009

(86) PCT No.: PCT/US2009/061141
§ 371 (c)(1),
(2), (4) Date: Apr. 20, 2011

(87) PCT Pub. No.: WO2010/048074
PCT Pub. Date: Apr. 29, 2010

(65) Prior Publication Data
US 2011/0202324 A1    Aug. 18, 2011

Related U.S. Application Data

(60) Provisional application No. 61/106,767, filed on Oct. 20, 2008.

(51) Int. Cl.
  A61N 5/10    (2006.01)
  G06F 17/50    (2006.01)
  A61B 6/03    (2006.01)

(52) U.S. Cl.
  CPC ........ A61N 5/1031 (2013.01); G06F 17/5009 (2013.01); *A61B 6/03* (2013.01); *A61N 2005/1034* (2013.01)

(58) Field of Classification Search
  USPC .......... 703/2, 6, 11, 12; 600/436; 378/64, 65, 378/70, 82
  See application file for complete search history.

(56) References Cited

U.S. PATENT DOCUMENTS

| 6,335,792 B1 * | 1/2002 | Tsuchiya ...................... 356/432 |
| 6,714,620 B2 * | 3/2004 | Caflisch et al. ................. 378/65 |
| 6,792,073 B2 * | 9/2004 | Deasy et al. ................... 378/65 |

(Continued)

OTHER PUBLICATIONS

A convolution method of calculating dose for 15-MV x rays, Mackie, et. al., Dept. of Medical Physics, Cross Cancer Institute, Received May 1, 1984, Accepted Aug. 14, 1984, pp. 1-9.*
Dose calculations using convolution and superposition principles: the orientation of dose spread kernels in divergent x-ray beams, Sharpe, et. al. Dept. of Medical Biophysics, The University of Western Ontario, Received Jun. 25, 1992, Accepted Jul. 2, 1993, pp. 1-10.*

(Continued)

*Primary Examiner* — David Silver
*Assistant Examiner* — Jay B Hann
(74) *Attorney, Agent, or Firm* — Gordon & Jacobson, PC

(57) ABSTRACT

A method for estimating a radiation dose and distribution for a target volume is provided. The method includes receiving a simulated dose array (606) describing a plurality of simulated dose values for a plurality of voxels in the target volume, generating an energy deposition coefficient function for the plurality of voxels (608), and obtaining a raw fluence array based at least on the simulated dose array and the energy deposition coefficient function (612). The method also includes generating an adjusted fluence array (613) based on the raw fluence array and at least one adjustment criteria, and generating an adjusted dose array (622) for the target volume based on the adjusted fluence array and the energy deposition coefficient function.

21 Claims, 9 Drawing Sheets

(56) References Cited

U.S. PATENT DOCUMENTS

| | | | |
|---|---|---|---|
| 7,519,150 B2* | 4/2009 | Romesberg et al. | 378/65 |
| 7,899,517 B2* | 3/2011 | Kindlein et al. | 600/427 |
| 7,945,022 B2* | 5/2011 | Nelms et al. | 378/65 |
| 8,125,813 B2* | 2/2012 | Nizin et al. | 365/65 |
| 8,494,115 B2* | 7/2013 | Hu et al. | 378/65 |
| 2002/0080912 A1* | 6/2002 | Mackie et al. | 378/21 |
| 2003/0030809 A1* | 2/2003 | Boas et al. | 356/432 |
| 2003/0212325 A1* | 11/2003 | Cotrutz et al. | 600/436 |
| 2004/0183461 A1* | 9/2004 | Kane et al. | 315/219 |
| 2006/0259282 A1* | 11/2006 | Failla et al. | 703/2 |
| 2007/0034812 A1* | 2/2007 | Ma et al. | 250/492.21 |
| 2007/0081629 A1* | 4/2007 | Yin et al. | 378/65 |
| 2008/0021682 A1* | 1/2008 | Holland | 703/5 |
| 2009/0063110 A1* | 3/2009 | Failla et al. | 703/2 |

OTHER PUBLICATIONS

Knöös, Tommy, et al. "Comparison of dose calculation algorithms for treatment planning in external photon beam therapy for clinical situations" Phys. Med. Biol., vol. 51, pp. 5785-5807 (2006) doi:10.1088/0031-9155/51/22/005.*

Miften, Moyed, et al. "Implementation of FFT convolution and multigrid superposition models in the FOCUS RTP system" Phys. Med. Biol., vol. 45, pp. 817-833 (2000).*

Rosenwald, Jean-Claude, et al. "Patient Dose Computation for Photon Beams" Chapter 26, pp. 559-585 (2007).*

Esch, Ann Van, et al. "Testing of the Analytical Anisotropic Algorithm for Photon Dose Calculation" Med. Phys., vol. 33, No. 11, pp. 4130-4148 (2006).*

* cited by examiner

100

200

300

600

600

SYSTEM AND METHODS FOR ACCELERATING SIMULATION OF RADIATION TREATMENT

CROSS REFERENCE TO RELATED APPLICATIONS

This application is a §371 national phase entry of International Application No. PCT/US2009/061141 entitled "SYSTEM AND METHODS FOR ACCELERATING SIMULATIONS OF RADIATION TREATMENT", filed Oct. 19, 2009, which claims priority to Provisional Application Ser. No. 61/106,767 entitled "SYSTEM AND METHODS FOR ACCELERATING SIMULATION OF RADIATION TREATMENT DOSE AND DISTRIBUTION", filed Oct. 20, 2008, both of which are herein incorporated by reference in their entirety.

STATEMENT REGARDING FEDERALLY SPONSORED RESEARCH

This invention was made with U.S. government support under Grant Number FA9550-04-1-0045 which was awarded by the Air Force Office of Scientific Research. The U.S. government has certain rights in the invention

FIELD OF THE INVENTION

The invention relates to simulating radiation treatment, and more specifically to systems and methods for accelerating simulation of radiation treatment.

BACKGROUND

The Monte Carlo method is generally considered an accurate method for predicting radiation dose distributions for planning radiation treatments. In particular, for large numbers of source radiation particles (typically above $10^7$), the Monte Carlo method typically produces an accurate representation of the dose distribution. For these reasons, the Monte Carlo method is typically preferred for the calculation of radiation dose in radiotherapy.

Unfortunately, the Monte Carlo method generally requires a large number of computations to generate a sufficient number of data points to provide an accurate representation of the resulting dose distribution in a patient. That is, the Monte Carlo method has no well-defined preset: "finish" time and a typical simulation results in dose distributions being continually calculated until the noise level falls below a level deemed acceptable by the user.

In some cases, radiotherapy treatment planners may wish to compare many dose distributions before selecting a final distribution for treatment. Therefore, there exists a need for dose modeling which is as accurate as the Monte Carlo method but which has greater computational efficiency than the Monte Carlo method.

SUMMARY

This Summary is provided to present a summary of the invention to briefly indicate the nature and substance of the invention. It is submitted with the understanding that it will not be used to interpret or limit the scope or meaning of the claims. Embodiments of the invention describe systems and methods for accelerating simulation of radiation treatments. In a first embodiment of the invention, a method for estimating a radiation dose and distribution for a target volume is provided. The method includes the steps of receiving a simulated dose array describing a plurality of simulated dose values for a plurality of voxels in the target volume, generating an energy deposition coefficient function for the plurality of voxels, and obtaining a raw fluence array based at least on the simulated dose array and the energy deposition coefficient function. The method also includes the steps of generating an adjusted fluence array based on the raw fluence array and at least one adjustment criteria, and generating an adjusted dose array for the target volume based on the adjusted fluence array and the energy deposition coefficient function.

In a second embodiment of the invention, a radiation treatment system is provided, including a storage element and a processing element. The storage element is configured for receiving a simulated dose array describing a plurality of simulated dose values for a plurality of voxels in a target volume includes one or more different compositions. The processing element is configured for planning a radiation treatment for a target volume includes one or more different compositions. The processing element is configured for generating an energy deposition coefficient function for the plurality of voxels, obtaining a raw fluence array based at least on the simulated dose array and the energy deposition coefficient function, generating an adjusted fluence array based on the raw fluence array and at least one adjustment criteria and generating an adjusted dose array for the target volume based on the adjusted fluence array and the energy deposition coefficient function.

In a third embodiment of the invention, a computer-readable medium, having stored thereon a computer program for planning a radiation treatment for a target volume includes a plurality of compositions is provided. The computer program includes a plurality of code sections. The code sections are executable by a computer for causing the computer to perform the steps of: receiving a Monte Carlo (simulated) dose array, the simulated dose array describing a plurality of simulated dose values for a plurality of voxels in the target volume; generating an energy deposition coefficient function for the plurality of voxels; obtaining a raw fluence array based at least on the simulated dose array and the composition coefficient array; generating an adjusted fluence array based on the raw fluence array and at least one adjustment criteria; and generating an adjusted dose array for the target volume based on the adjusted fluence array and the composition coefficient array.

In a fourth embodiment of the invention, a system for estimating an impact to a target volume of one or more particles travelling therethrough. The system includes a storage element for receiving a simulated deposition array, the simulated deposition array describing a plurality simulated deposition values for a plurality of voxels in a target volume includes one or more different compositions. The system also includes a processing element. The processing element is configured for generating an energy deposition coefficient function for the plurality of voxels, obtaining a raw fluence array based at least on the simulated deposition array and the energy deposition coefficient function, generating an adjusted fluence array based on the raw fluence array and at least one adjustment criteria, and generating at least one adjusted deposition array for the target volume based on the adjusted fluence array and the energy deposition coefficient function.

DETAILED DESCRIPTION

Figure 1:
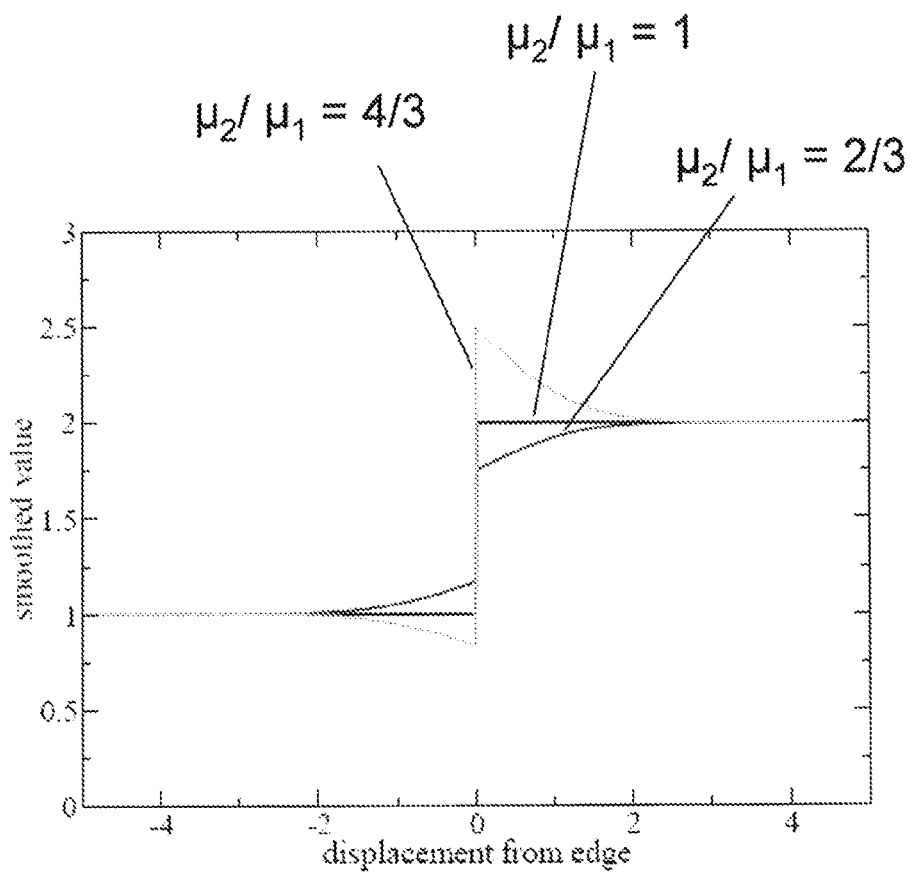
FIG. 1 is a plot of exemplary smoothing results for various exemplary value differences at a boundary between different regions of the target volume according to an embodiment of the invention.

The invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should generally be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The invention is not limited by the illustrated ordering of acts or events, as some acts may occur in different orders and/or concurrently with other acts or events. Furthermore, not all illustrated acts or events are required to implement a methodology in accordance with the invention.

Computing radiation dose estimates in preparation for radiation therapy in patients is a critical part of both the treatment process and the development of new modalities. Currently, a significant amount of radiotherapy treatment planning is carried out using quasi-analytic transport simulation programs provided by the manufacturer of the therapy equipment. Such simulation programs are typically tuned to the specific applications, and are generally computationally efficient. However, as the target volume is altered in composition and/or arrangement, extensive retuning can be required for such simulation programs to provide computational efficiency for the altered target volume. As used here, the term "target volume" refers to the volume of the organism or object being irradiated. In some cases, retuning is avoided by providing more complex simulation programs, such as Monte Carlo simulation programs, that function by directly tracing the progress of a large sample of incoming particles and statistically determining where and how they deposit energy. Even though such simulation programs can be easily adapted to new situations, the computational requirements generally limit the widespread use of such simulation programs.

In general, the limiting term in the quality of a Monte Carlo transport calculation and other types of transport calculations is the convergence of the statistical errors roughly as the square root of the computational effort. Thus, to gain a tenfold improvement in statistical quality generally requires one hundred fold increase in effort. Therefore, any technique which can be applied to improve the statistical smoothness of the results for a given number of events processed (called a variance reduction technique) is then very valuable. For example, in Monte Carlo simulation-based radiotherapy planning, the commonly used variance reduction techniques can be classified into two types: (1) techniques for weighting the particles considered in the Monte Carlo simulation to concentrate computational time on those which have the biggest effect on the dose without introducing bias and (2) techniques that post-process the final dose distribution, typically through some form of smoothing. Weighting techniques can produce an appreciable improvement in run time; they generally tend to be problem and implementation specific. In contrast the post-processing techniques are more generally applicable, but they have the drawback that as the computed dose becomes very smooth there is a loss of spatial resolution. Therefore, a trade-off exists between the amount of variance reduction possible and the blurring of sharp features in the dose distribution. Fundamentally, this is because the deposited dose is not a smooth function in an inhomogeneous volume, rather the sharp edges in the composition appear as sharp edges in the deposited dose.

Accordingly, the various embodiments of the invention provide systems and method for accelerating radiation treatment simulation. The term "radiation treatment", as used herein, refers to any type of intentional radiation exposure, such as during radiographic diagnostic (e.g. computed axial tomography) or therapeutic procedures (e.g. radiotherapy). One aspect of the invention is to provide simulation methods for computing radiation dose and radiation dose distribution in which the simulation is separated into two components, one of which contains composition information related to the discontinuities in composition between regions in the target volume, which is not to be smoothed, and the other of which contains a continuous function related to radiation flux or fluence which can be aggressively smoothed. After smoothing, the composition information can be re-introduced to restore the expected discontinuities in the result. This composition information can be an approximation of the mass-energy transport coefficient $\mu_{en}$ adjusted to improve the smoothing process. As a result, the equation for dose is $D(\bar{r})=\mu_{en}(\bar{r})\cdot\phi(\bar{r})$, where $\phi(\bar{r})$ is the sum over all particles of interest to the simulation of the scalar magnitude of the radiation fluence, and $\mu_{en}(\bar{r})$ is the local absorption of the composition.

Although in some exemplary embodiments of the invention, the simulation methods will be described with respect to modeling of a particular type of particle from a radiation source, such exemplary embodiments are presented by way of example and not by way of limitation. The various embodiments of the invention are equally applicable to the simulation of any type of particle emitted from a radiation source, including photons, electrons, ionized atoms and molecules, and antiprotons to name a few.

The Present Inventors have discovered even modest improvements in smoothing techniques can provide significant gains in statistical significance. For example, if transport occurs in a 3-dimensional geometry, doubling the size of the volume over which the smoothing kernel operates results in $2^3$ (8) times more information being applied to compute the value of the function at a given point. As a result, smoothing lengths 10 times larger than in conventional methods can be used, resulting in 1,000 fold run time reductions. Therefore, as long as this smoothing does not result in inconsistent information, resulting in bias of the computed value at a point, the smoothing can be applied over as large a volume. Therefore, in the various embodiments of the invention, a technique is provided for solving the issue of inconsistent information being brought in due to composition boundaries while still allowing large smoothing kernels to accelerate dose distribution calculations sufficiently that they become computationally efficient for routine radiotherapy planning calculations across a full spectrum of treatment modalities.

Fundamentally, the transport of a flux of particles through a medium is controlled by the scattering, absorption, annihilation, creation and emission of particles. Normally, a full treatment planning methodology requires integration of the appropriate transport equations via, for example, a Monte Carlo integrator. However, the computational expense of this approach due to photons being absorbed and scattered in discrete events and Poisson counting statistics determining the noise level can be high.

Instead, in the various embodiments of the invention, it is generally assumed that all the transport equation solutions need have one particular characteristic, which is that the fluence of each species is a continuous function of position. Furthermore, it is assumed that the scale lengths for changes in the fluence are long compared to the scale lengths of interest in the models. Such assumptions are generally valid, since radiotherapy is typically performed with types of radiation which can be transported over a distance of at least a few centimeters without strong attenuation for treating tumors of finite size.

In the various embodiments of the invention, an un-smoothed dose map $\{D(\bar{r})\}$ is obtained from a simulator, such as Monte Carlo dose simulator, which comprises of the dose in each of a set of voxels in a discrete grid. In some embodiments of the invention, the un-smoothed dose map can be generated by performing a pre-determined number of simulation runs. In other embodiments of the invention, a high noise level can be specified. In either case, the noise in the unsmoothed dose map is significantly higher than would be desired for conventional radiotherapy planning, albeit a large smoothing volume is typically required. The term "smoothing volume", as used herein, refers to the width of the smoothing kernel being used. In the various embodiments of the invention, the noise that can be permitted in the unsmoothed dose map can larger by approximately a factor of the square root ratio of the smoothing volume being used versus the smoothing volume used in conventional techniques. For example, a conventional smoothing volume is approximately 10 to 100 times smaller than a smoothing volume in accordance with the various embodiments of the invention. Accordingly, 3 to 10 times more noise can be permitted for a dose map to be used with the various embodiments of the invention.

In general the unsmoothed dose map can have a set of statistical errors $\{\sigma(\bar{r})\}$ and a set of coefficients $\{\mu(\bar{r})\}$ which describe the mean energy deposition per fluence at the specified point. In simple cases, this set of coefficient will be dependent only on the composition at a point, so the coefficients can be expressed as $\{\mu(M_k(\bar{r}))\}$ where $\{M_k\}$ is a set of known compositions which are in the target, and $M_k(\bar{r})$ indicates that the voxel at $\bar{r}$ is occupied by the composition with index k. In some embodiments of the invention, $\mu$ can be provided a function of composition with a smooth dependence on position to accommodate changes in the primary beam spectrum as it propagates. In some embodiments of the invention, $\mu$ can be provided as a function of the particle type(s) of interest in the simulation.

From the set of points in the dose map, a scaled dose map can be derived, which is effectively a fluence map, $$\phi(\bar{r})=D(\bar{r})/\mu(\bar{r}) \qquad (1)$$

and a map of statistical weights $w(\bar{r})$ for each point. A discrete, weighted convolution can be performed and can replace the scaling by $\mu$ in the smoothed result to get:

$$\langle D(\vec{r})\rangle = \mu(\vec{r}) \frac{\sum_{\vec{r}'} \phi(\vec{r}+\vec{r}')w(\vec{r}+\vec{r}')K(\vec{r}')}{\sum_{\vec{r}'} w(\vec{r}+\vec{r}')K(\vec{r}')} \qquad (2)$$

where $K(\bar{r})'$ is a smoothing convolution kernel. In the examples described below, $K(\bar{r}')$ is chosen to be Gaussian, and $\bar{r}$ runs over voxels for which $K(\bar{r}')$ is non-zero. However, the various embodiments of the invention are not limited to Gaussian kernels and any other type of smoothing kernel can be used with the various embodiments of the invention.

Although most tissue types only have a small range of dose absorbed depending on their density and a non-weighted sum would generally work, tissue-air boundaries are a special case. In air, the dose absorbed is typically very small, and in the simulation, the resulting number is extremely uncertain. That is, the dose values are associated with a statistical variation or uncertainty. Therefore, if the sum is weighted so that the reciprocal of $\mu$ is removed from the numerator of the sum, and appears linearly in the denominator, the regions of very low $\mu$ are de-emphasized, and the result becomes quite insensitive to this effect. For example, $w(\bar{r})=\mu(\bar{r})$ can be used, which generally has the desired characteristics. However, the various embodiments of the invention are not limited in this regard and, alternative forms for $w(\bar{r})$ can be used.

Bias

Although smoothing techniques typically introduce some type of bias, the various embodiments of the invention provide for little or no bias. That is, equation (2) provides an unbiased estimate of the local dose, which is not strongly dependent on the choice of coefficients $\{\mu\}$. For example, in a region with constant $\mu$, equation (2) reduces to $$\langle D(\vec{r})\rangle = \frac{\sum_{\vec{r}'} D(\vec{r}+\vec{r}')w(\vec{r}+\vec{r}')K(\vec{r}')}{\sum_{\vec{r}'} w(\vec{r}+\vec{r}')K(\vec{r}')} \quad (3)$$

since the values of μ are constant inside the summation, and can be factored out. As a result, equation (3) is not dependent on μ, so in regions of uniform composition, the result is just a weighted mean. If w is independent of D, and depends only on μ, this simplifies equation (3) even further in regions of constant μ to $$\langle D(\vec{r})\rangle = \frac{\sum_{\vec{r}'} D(\vec{r}+\vec{r}')K(\vec{r}')}{\sum_{\vec{r}'} K(\vec{r}')} \quad (4)$$

which is just the smoothed mean of the data at the point, devoid of bias.

Edge Effects

As previously described, μ can vary for different regions of the target volume. However, in the various embodiments of the invention, such variations have little effect on the subsequent smoothing. For example, in a 1-dimensional case consider a simple step function $\mu(x)=1$ for x<0 and $\mu(x)=\mu_1$ for x>0. Also consider the case in which $D(x)=D_0 v(x)$ where $v(x)=1$ for x<0 and $n(x)=\mu_2$ for x>0, and all the weights are 1. Then, $\phi(x)=1$ for x<0 and $\phi(x)=\mu_2/\mu_1$ for x>0, $$\langle D(x)\rangle = \frac{D_0}{\sqrt{2\pi}\,\sigma}\mu(x)\int_{-\infty}^{\infty}\frac{1}{\mu(x-x')}D(x-x')e^{-x'^2/2\sigma^2}\,dx' \quad (5)$$

$$\langle D(x)\rangle = \frac{1}{2}\mu(x)D_0\left[\left(\frac{\mu_2}{\mu_1}+1\right)+\left(\frac{\mu_2}{\mu_1}-1\right)erf\!\left(\frac{x}{\sqrt{2}\,\sigma}\right)\right]$$

which is plotted in FIG. 1. FIG. 1 is a plot of exemplary smoothing results for various exemplary μ value differences at a boundary between different regions of the target volume according to an embodiment of the invention. As can be seen both analytically and graphically in exemplary results shown FIG. 1, the smoothed value generally converges to the correct value far from a step edge. The above derivation also shows that for the correct value of μ no bias is generally introduced on either side of a step.

Numerical Implementation

In the various embodiments of the invention, equation (2) provides a formal solution. If the kernel $K(\vec{r})$ is non-zero on a small number of voxels around a point, equation (2) can be evaluated directly. As the number of non-zero terms becomes large, a large number of computations are required. For example, in the test cases described below, the kernel was defined in a 21×21×21 box with 9261 elements. Thus, each smoothed point in the output requires a few times this many adds and multiplies, which leads to a very large operation count.

However, as previously described, equation (2) is essentially a modified convolution. Therefore, in some embodiments of the invention, the sum can be treated as the ratio of two conventional convolutions, each of which can be carried out via Fourier transform methods very efficiently. Although such an evaluation normally requires some adjustments to prevent the edges being improperly smoothed or wrapped around to other edges, the way the convolution is presented in equation (2) provides an opportunity to prevent this with essentially no extra effort. That is, because the denominator of equation (2) a convolution over the statistical weights associated with the convolution over φ in the numerator, real data φ and the weight array w can be embedded in a padding arrays of zeros prior to carrying out the operation as described. The reduced weight introduced by these zeros at the edges properly compensates for the zero data being brought into the numerator, resulting in the convolution proceeding correctly right to the edges of the target volume. However, because the edges contain a smaller volume of valid data, the results will necessarily be noisier. At a simple plane edge, the noise will be increased by $\sqrt{2}$, since only half the kernel lies in a region with non-zero weight. At a full 3-dimensional corner, the noise is increased by $\sqrt{8}$, since only one octant of the kernel cube will lie in the valid region.

Therefore, in some embodiments of the invention the following numerical implementation can be used. First, let {l, m, n} be the set of sizes of the real data set for the target volume in the x, y, and z directions, respectively. Second, assuming a Gaussian kernel, with widths projected into the directions of the data grid of $\sigma_x$, $\sigma_y$, $\sigma_z$, three arrays {ρ}, {W} and {K'} filled with zeros, can be created. In such embodiments of the invention, single-precision arrays can be used but are not necessary. The arrays should generally have sizes of at least [l+3$\sigma_x$, m+3$\sigma_y$, n+3$\sigma_z$], with each size padded up to the next reasonable size for Fast-Fourier-Transform (FFT) computation. Afterwards φw, w, and the kernel K can be embedded in {ρ}, {W} and {K'}, respectively.

Once the arrays {ρ}, {W} and {K'} are constructed, the discrete, real Fourier transform of each can be computed, designated herein as {$\hat{\rho}$}, {$\hat{W}$}, and {$\hat{K}$}, respectively. The smoothed result can then be expressed via the usual convolution theorem result that the product of the transforms is the transform of the convolved result, so $$\langle D(\vec{r})\rangle = \mu(\vec{r})\frac{\widetilde{\hat{\rho}\hat{K}'}}{\widetilde{\hat{W}\hat{K}'}} \quad (6)$$

where the wide tilde operators represent the inverse FFT. The array <D($\vec{r}$)> will contain valid data embedded the same way that φw was embedded in ρ, and invalid data in the regions which were left zero by the embedding and padding operation. In practice, the speed gain over utilizing equation (2) directly is generally very large.

Anisotropic and Inhomogeneous Kernels

In some embodiments of the invention, the dose can be computed as the result of multiple nearly collimated beams of finite size. In these instances, very smooth dependence of the fluence in the direction of propagation of the beam can be used advantageously while providing for structure in the target volume transverse to the beam. Accordingly, in some embodiments of the invention, which comprise kernels which are anisotropic (so that $K(\vec{r})$ cannot be simplified to K(r)) can be provided. In such embodiments of the invention, no modification of equation (2) is generally necessary and can always generally be computed, for example, by the transform methods described above. An anisotropic kernel can be very useful in situations in which, for example, the sample is being irradiated with a beam with sharp edges, and behavior near the beam edges is important. To handle this, a smoothing kernel can be selected which has a large smoothing length in the direction of propagation of the beam, and a somewhat shorter smoothing length perpendicular to the beam. Typically, then, K(r̄) becomes a uniaxial or triaxial Gaussian ellipsoid with its longest axis in the direction of beam propagation. However, the computation of equation (2) is generally unaffected by this generalization.

In contrast, in embodiments of the invention where the kernels are inhomogeneous some adjustment can be needed. That is, if kernels in which the smoothing function vary depending on the region in space being smoothed a slight generalization of equation (2) and can no longer be considered a simple convolution. However, such a generalization can provide important benefits. This case results in a modified version of equation (2), $$\langle D(\vec{r}) \rangle = \mu(\vec{r}) \frac{\sum_{\vec{r}'} \phi(\vec{r} + \vec{r}') w(\vec{r} + \vec{r}') K(\vec{r}, \vec{r}')}{\sum_{\vec{r}'} w(\vec{r} + \vec{r}') K(\vec{r}, \vec{r}')} \quad (7)$$

which is no longer exactly a convolution, and cannot be computed by transform techniques, and is therefore very expensive to compute. However, such a form allows one to choose a very large smoothing kernel in all directions in regions where the incident beam (for example) is uniform and allows shrinking of the kernel near edges of the beam to preserve the real structure of the target volume.

An alternative approach to the use of inhomogeneous kernels is suggested by the difference in computation time between the transform-based solutions possible with homogeneous kernels and the sum needed for the inhomogeneous case. Accordingly, in some embodiments of the invention, smoothing can be carried out using kernels of a few different sizes. Afterwards, the resulting smoothed data sets are spliced together. In such embodiments of the invention, a broad kernel can be used regions within the beam and the finer kernel can be used at the edges of the beam.

Optimization of Coefficients (μ)

In the various embodiments of the invention, the coefficients μ can be obtained in several ways. In some embodiments of the invention, coefficients can be determined empirically or based on published values for mass attenuation. However, in other embodiments of the invention, an analytic method can be used to produce an "optimum" set of coefficients. In these embodiments of the invention, the coefficient can be analytically derived such that the differences which occur between voxels at composition boundaries are minimized. That is, minimizing the quantity $D_{m,i}/\mu_m - D_{n,j}/\mu_n$, where $D_{m,i}$ is the dose deposited to some $i^{th}$ voxel in composition m, and $\mu_m$ is the coefficient assigned to composition m, for all pairs of neighboring voxels which lie on a interface between two regions of different compositions in the target volume.

In an ideal situation, $D_{m,i}/\mu_m - D_{n,j}/\mu_n = 0$. However, due to factors such as the error in the dose calculated for individual voxels or attenuation of the beam as it passes through tissue, obtaining a solution is difficult, if not impossible. Instead, the embodiments of the invention deriving coefficients analytically, a set of ratios is provided to minimize the deviation from this goal.

Specifically, in some embodiments of the invention, the ratios can be calculated from a set of equations of the form Ax=b:

$$\begin{bmatrix} \frac{D_{0,i}}{\sigma_{i,j}} & 0 & \frac{-D_{2,j}}{\sigma_{i,j}} & 0 & \cdots \\ \frac{D_{0,k}}{\sigma_{k,l}} & \frac{-D_{1,l}}{\sigma_{k,l}} & 0 & 0 & \cdots \\ \vdots & \vdots & \vdots & \vdots & \\ 1 & 0 & 0 & 0 & \cdots \end{bmatrix} \begin{bmatrix} \frac{1}{\mu_0} \\ \frac{1}{\mu_1} \\ \frac{1}{\mu_2} \\ \frac{1}{\mu_3} \\ \vdots \end{bmatrix} = \begin{bmatrix} 0 \\ 0 \\ \vdots \\ 1 \end{bmatrix} \quad (8)$$

where each term has had a statistical weight $1/\sigma_{i,j}^2$ attached to it, given by the combination of the statistical error associated of each of the voxels which make up the boundary. The last row of the design matrix and solution vector is added to assure that the system has a unique solution. Otherwise, with a solution vector of all zeros, any linear multiple of the solution would also be valid. As a result, the system of equations represented in equation (8) is non-singular, and the ratios of the coefficients can be computed in post-processing.

Furthermore, since equation (8) represents an over-determined system of equations, an optimized set of weights can be obtained which provides least squares residuals. In general, the matrices in equation (8) are expected to be well behaved and optimal solution can be determined by evaluating $A^T A x = A^T b$. In embodiments of the invention including poorly determined parameters in the set, a singular-value-decomposition (SVD) can be provided to improve the solution. However that the values of coefficients returned are likely to depend only on the compositions involved and (usually rather weakly) on the energy spectrum of the incoming beam. This means that a set of coefficients can be derived from a representative solution and then transferred to transport problems of a similar nature. Also, it means that in general the $\mu_m$ might vary slightly along a beam or otherwise as a function of location.

Figure 2:
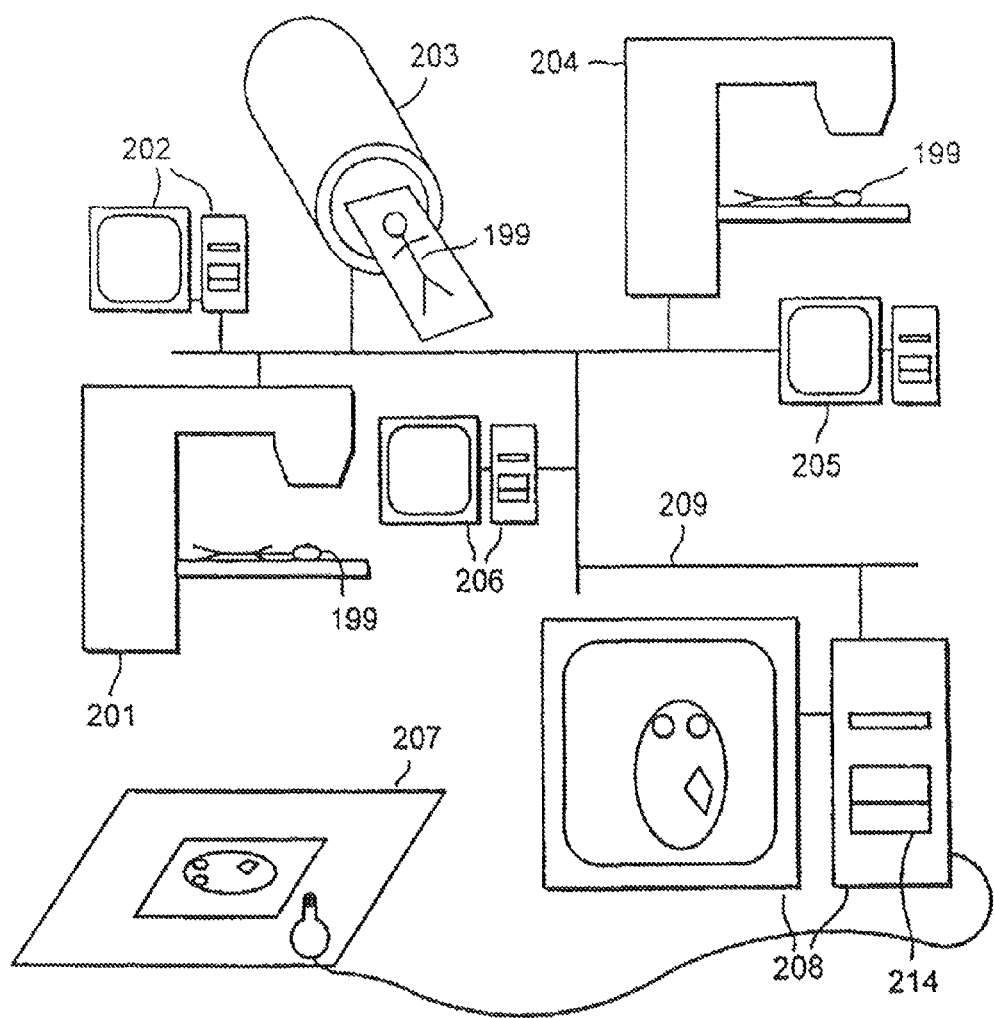
FIG. 2 shows a schematic of an exemplary radiotherapy treatment system configured for implementing one or more methodologies in accordance with the various embodiments of the invention.

FIG. 2 shows a schematic of an exemplary radiotherapy treatment system 200 configured for implementing one or more methodologies in accordance with the various embodiments of the invention. Although FIGS. 2, 3, 4 and 7 will be described with respect to a Monte Carlo simulator, the invention is not limited in this regard and the various embodiments of the invention are equally applicable to other simulation methods. In FIG. 2, a network 209 connects a computed tomography (CT) scanner 203, a radiotherapy treatment simulator 204 and a radiotherapy treatment machine 201, together with their associated computer controllers 202, 205, 206. However, the invention is not limited solely to networked treatment systems. One of ordinary skill in the art will recognize that the network 209 in exemplary system 200 is provided to facilitate the exchange of data between the various components. Accordingly, any other method of exchanging data, including manual transfer or entry of data can be used in the various embodiments of the invention. In FIG. 2, a radiotherapy treatment planning computer 208, on which a Monte Carlo simulator 340 runs is also connected to the network 209. The radiotherapy treatment planning computer 208 can draw data from the CT scanner 203 concerning the outline and density of a patient 199, or such information may be entered directly into the radiotherapy treatment planning computer 208 using a digitizer 207. A user interface 240 can be used to set up a treatment plan, such as deciding where radiotherapy beams should generally be placed, their shape and evaluating whether any beam blocking is required. The radiotherapy treatment planning computer 208 uses this information, together with stored beam properties and patient tissue data to generate a treatment plan. This process is described in more detail later. A radiographer can then examine the plan on the treatment simulator controller 205 and if the treatment plan is satisfactory the patient can be treated on the treatment machine 201.

One of ordinary skill in the art will recognize that system 200 is only one possible configuration for a radiotherapy system. Accordingly, the various embodiments of the invention are equally applicable to different arrangements and configurations for the various components in system 200. For example, in some embodiments of the invention, each of the components can operate as a set of local or distributed resources. Furthermore, it is also within the scope of the invention to combine the functionality of one or more of the components in system 200 into a single component.

Figure 3:
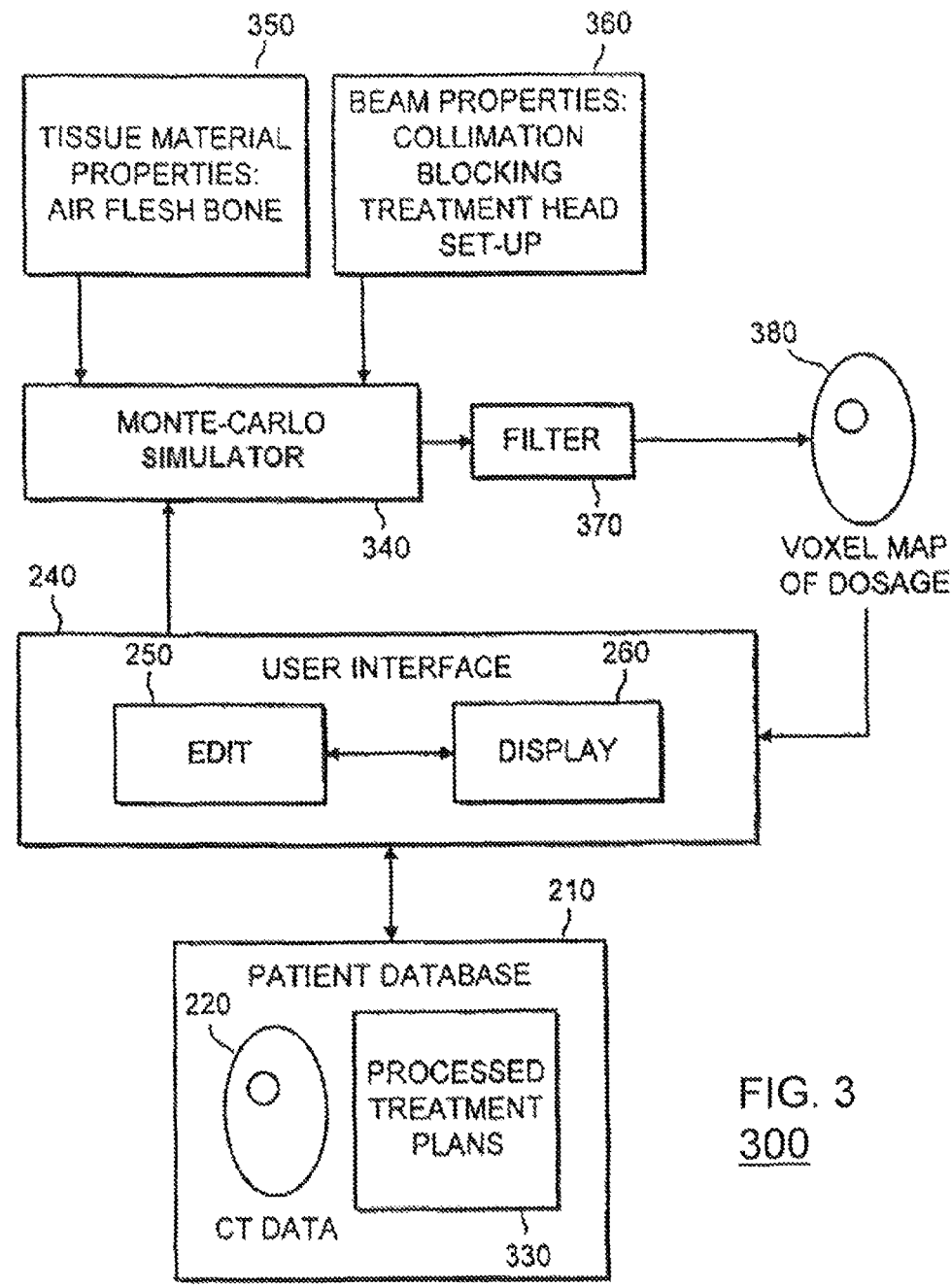
FIG. 3 shows a block diagram depicting schematically the operation of the radiotherapy system shown in FIG. 2.

FIG. 3 shows a block diagram 300 depicting schematically the operation of the radiotherapy system 200 shown in FIG. 2. The patient database 210 and the user interface 240 are substantially the same as in the prior art system, although the processed treatment plans 330 comprise treatment parameters together with a voxel map 380 of the dose distribution. From the user's point of view, therefore the two systems are very similar. Once the treatment parameters have been set by the user the energy or dosage deposited in each voxel is calculated by a Monte Carlo simulator 340. This simulator 340 uses pre-processed data 350 concerning the composition properties of typical patient tissues and other materials in the target volume and pre-processed data 360 concerning the effect of collimation and treatment head set-up on the beam. The Monte Carlo simulator 340 performs simulation runs until it reaches a pre-set statistical variance or until a pre-defined number of simulation runs have be completed.

The output from the Monte Carlo simulator 340 can be passed to a low pass digital filter 370. After a short run-time the statistical uncertainty in the simulation data output from the Monte Carlo simulation 340 will be large, but since the error at each voxel will be independent, filtering can be used to suppress the uncertainty at all points in the three-dimensional data set. To compensate for increased resolution the filter 370 has a variable aperture which may be tuned to the length scale required for each voxel. Varying this aperture increases the effectiveness of filtering for high resolution data, at least partly offsetting the otherwise large increase in computation time needed. In general, the filter 370 output can comprises a voxel map of the dosage 380 which can then be displayed by the display 260 in the user interface 240. The planner can then consider whether the plan meets clinical objectives and reiterate the planning process as necessary.

Figure 4:
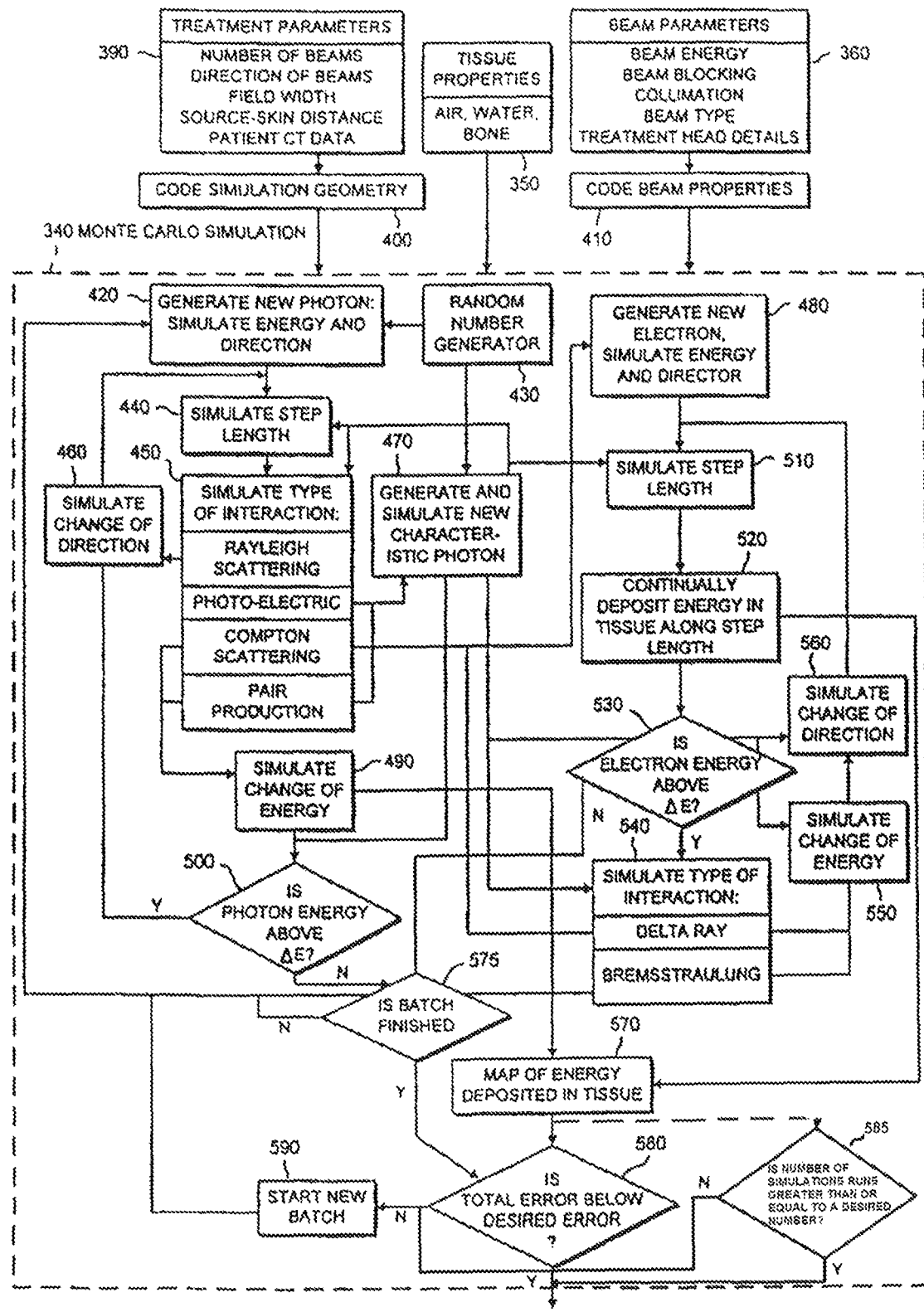
FIG. 4 shows a block diagram depicting the operation of the Monte Carlo simulator in FIGS. 2 and 3.

FIG. 4 shows a block diagram 400 depicting the operation of the Monte Carlo simulator in FIGS. 2 and 3. Information such as treatment parameters 390, tissue properties 350 and beam parameters 360 are input into the simulation kernel. This information may be pre-processed such as in the case of the tissue properties 350, or, as m the case of the treatment parameters 390 require coding in a step 400. The step 400 translates the simulation geometry into a form suitable for use by the Monte Carlo simulator 340, while a different step 410 completes a similar procedure for the beam properties 360.

The Monte Carlo simulation 340 continually generates and simulates the life of different incident particles, whilst the variance of the energy deposited in the image remains above a user-set threshold. For illustrative purposes, the remainder of FIG. 4 will be described with respect to incident photons. The general procedure is to draw up a probability function depending on beam and patient properties and to determine randomly which of a particular event occurs. Firstly in a step 420 the simulator 340 generates a new photon. This requires simulation of the new photon's energy and direction, given the beam parameters 360. Information from beam parameter coding step 410 is used to set up a probability function which determines the likelihood of the photon possessing a particular value for energy or direction. This particular value for the photon is simulated by using a random number generator 430. Any type of random number generator suitable for Monte Carlo simulator can be used with the various embodiments of the invention.

Once a new photon is generated the length of space that it transverses before undergoing an interaction is simulated in a simulation step 440. This will depend on the treatment parameters 390, and the tissue properties 350. Next, the type of interaction undergone by the photon is simulated in a simulation step 450. The probability function for different types of interactions will depend on the properties of the individual photon and the composition properties of the medium in which the interaction occurs.

The next step in the simulation will depend on the type of interaction undergone. For example, for classical (or Rayleigh) scattering there is no change in the energy of the photon and the Monte Carlo kernel moves on a step 460 to simulate the change of direction of the photon before returning to the previous step 440 to simulate the step length before a further interaction. For a photoelectric interaction, Compton or pair production interaction energy is deposited into the tissue and the kernel records this in a map 570 comprising of the energy deposited in the tissue 570. Additionally an electron is generated for the simulation in step 480 with energy and direction properties which are physically determined by the type of interaction that generated the electron.

For pair production and Compton interactions a change in energy of the photon is also generally simulated in a step 490. If the photon energy is sufficient for another interaction to take place (i.e., the photon has not been absorbed) the change in direction is simulated in the change of direction step 460, the probability function of which will again depend on the type of interaction occurring. If a photo-electric interaction occurs a characteristic photon can be generated in a simulation step 470 which if its energy is found to be sufficient in another step 500 may interact further in its turn.

Electrons generated by the Compton interactions, pair production processes, or photo-electric processes are simulated in a further step 480. Their energy and direction probability functions will be calculated by the type of interaction and the properties of the parent photon and randomly simulated. The step length until a large interaction involving the electron is then simulated in another step 510. Small interactions, which take place along the entire length of the step length, are simplified to a continual constant deposition of energy and simulated in an energy deposition simulation step 520 which transmits that data to the map of the total energy or dosage deposited in the tissue 570.

In a following step 530 the energy of the electron is evaluated. The electron may have run out of energy before a large interaction occurs, in which case its simulated life is over and the algorithm moves to an evaluation step 575. However, if there is sufficient energy for a large interaction to occur, the type of interaction is randomly determined in another simulation step 540. If a delta ray results, another electron is generated in a following step 480 while if Bremsstrahlung radiation occurs another photon is generated in the first simulation step 420. In either case the change in energy of the electron simulated in a following simulation step 550 and the change in direction of the electron in a further step 560. The probability functions shaping the results from these steps are determined by the original electron properties and whether a delta ray was produced or Bremsstrahlung radiation occurred. Once the original incident photon and all interaction products have been fully simulated such that their energy has dissipated, another incident photon is generated in the simulation step 420. Normally a minimum number of photons are generated, and divided into a plurality of batches, such as five or ten.

In some embodiments of the invention, the mean and standard deviation amongst all the batches is calculated evaluated in a simulation step 575, and used to calculate the statistical error of the overall result in a simulation step 580. If the error is too high, a further batch is started in a simulation step 590 and the process is repeated until a desired error is reached. If not, the simulation is considered to be finished and the map of the energy or dosage deposited in the tissue 570 is passed to the filter means 370. In such embodiments of the invention, the desired error is significantly higher than the error normally required for radiotherapy planning, as previously described. Alternatively, to limit the number of simulation runs, if the number of simulation runs is greater than or equal to a pre-determined number in step 585, the simulation is consider to be finished and the map of the energy or dosage deposited in the tissue 570 is passed to the filter means 370. If an insufficient number of runs have been completed, a further batch is started in a simulation step 590 and the process is repeated until pre-determined number of runs reached at step 585.

Figure 5:
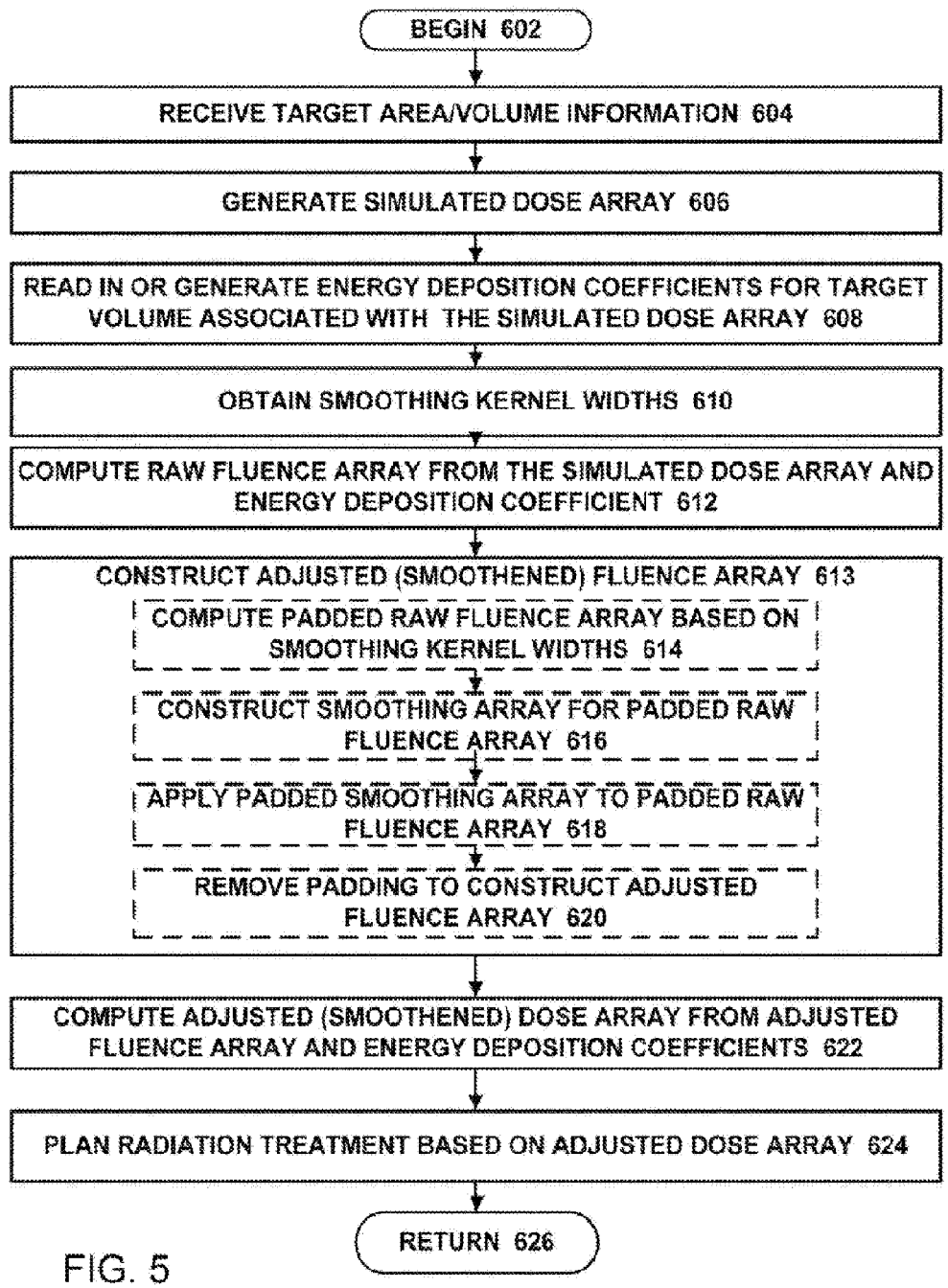
FIG. 5 is a flowchart of steps in an exemplary method for planning radiation treatments in accordance with an embodiment of the invention.

FIG. 5 is a flowchart of steps in an exemplary method 600 for planning radiation treatments in accordance with an embodiment of the invention. The method can begin in step 602 and continue on to step 604. In step 604 target area or target volume information is received. That is, as shown in FIG. 4, properties of the materials in the target volume, as well as the locations of the materials in the target volume can be provided. Afterwards, in step 606, a simulated dose array can be generated, for example using a Monte Carlo simulation, such as the simulation described above in FIG. 4. Once the simulated dose array is generated in step 606, the energy deposition coefficients ($\mu_m$'s) for the dose array can be generated in during step 608. Alternatively, the dose array can be pre-tabulated or pre-generated and read in during step 608. As previously described, such coefficients can be developed based on known or empirically collected values. Alternatively, the coefficients be based on a least squares approximation, such as that described above with respect to equation (8) being derived either from the treatment planning problem at hand or a problem of a similar nature with respect to tissue types, radiation type and energy. Subsequently, or in combination with step 608, adjustment criteria (e.g., smoothing kernel widths) for the smoothing kernels can be obtained in step 610. As previously described, any smoothing widths can be provided for any type of smoothing kernel. However, depending on the type of kernel and widths (anisotropic or non-homogenous kernels), subsequent computation can be affected, as described above with respect to equation (7).

Once the energy deposition coefficients are generated in step 608, the raw fluence array can be computed in step 612 and an adjusted fluence array can be constructed in step 613 by smoothing the raw fluence array computed in step 612. In step 613, any type of smoothing technique can be used to generate the adjusted fluence array. However, in some embodiments, padded array techniques can be used, as described above, to construct the adjusted fluence array.

For example, as shown in FIG. 5, during step 613, a padded raw fluence array can be generated in step 614. As previously described, the dimension of the padded raw fluence array can be based on the kernel widths provided in step 610. Afterwards, in step 616, a padded smoothing array can be generated so as to be dimensionally compatible with the padded raw fluence array and is combined with the padded raw fluence array in step 618 to produce the padded adjusted fluence array, i.e., a smoothened fluence array. Afterwards, in step 620, an unpadded adjusted fluence array can be constructed from the padded adjusted fluence array. That is, the zeros used for padding are removed.

Afterwards, the adjusted fluence array constructed during step 613 can be recombined with the energy deposition coefficients to compute an adjusted dose array in step 622. Afterwards, the adjusted dose array can be use to plan a radiation treatment for the target volume in step 624. For example, the adjusted dose array can be combined with a set of weights estimated to provide the desired dose distribution. The method can then end in step 626 and resume previous processing.

Figure 6:
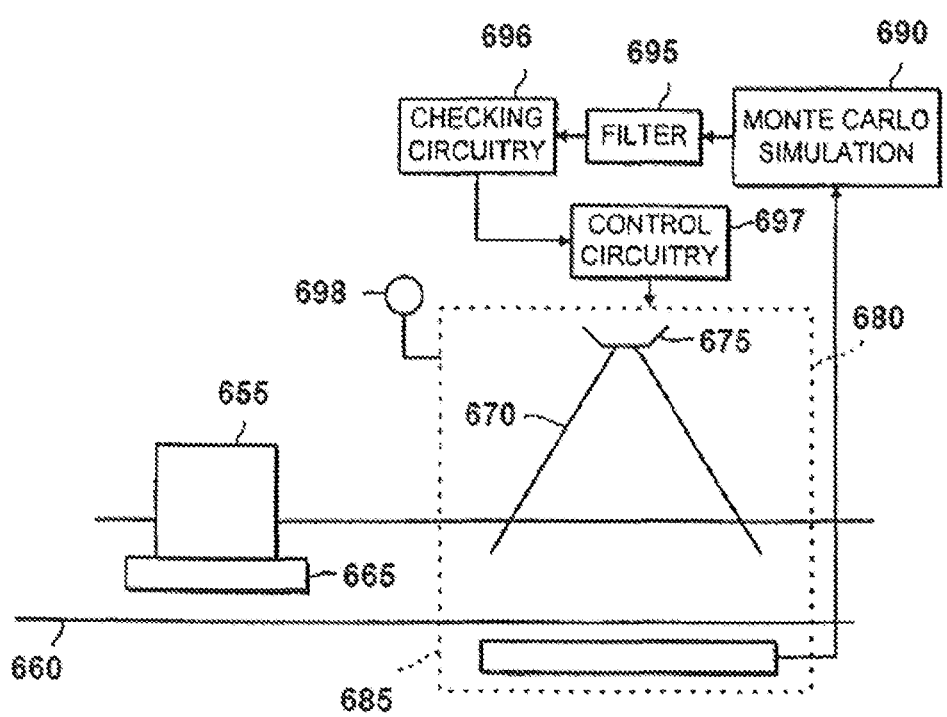
FIG. 6 shows a schematic of an exemplary sterilizer system configured for sterilizing foodstuffs, medical items, or other objects in accordance with the various embodiments of the invention.

However, the invention is not limited solely to radiotherapy applications. Rather the various embodiments of the invention are equally applicable in any system where the radiation dose for a target volume needs to be configured accurately For example, FIG. 6 shows a schematic of an exemplary sterilizer system 650 configured for sterilizing foodstuffs, medical items, or other objects in accordance with the various embodiments of the invention. As shown in FIG. 6, a container 655, with a volume which can vary according to changeovers and other factors upstream in a manufacturing process, is packaged and carried on a conveyor belt 660 by a pallet 665. This container is sterilized by an x-ray beam 670, derived from a rotatable x-ray head 675 in order, for example, to kill bacteria and elongate the shelf life of a foodstuff.

To attain good standards of food or medical safety and hygiene using this method the whole volume within the container 655 should generally be irradiated past a threshold value. Excess radiation, however could cause the contents itself to degrade. It is therefore important that a reasonable uniformity of irradiation, past a threshold value, is attained throughout the volume of the container 655. Modern factories, however, require flexible operations so that changing over to different products (which may have different densities and therefore require different irradiation times) may be simply and speedily accomplished. In this instance the sterilizer area 680 is sited substantially at the end of the production process before the pallets 665 are loaded onto transport vehicles. A sufficient uniform dose should generally be received by each container 655 regardless of its volume. To maintain throughput, however, the sterilization process should generally be accomplished within a reasonable time.

When a pallet arrives in the sterilizer area 680, which comprises a closed box screened with lead the x-ray head 675, set at a field size sufficient to irradiate the largest possible container 655, first gives a brief burst of x-rays 670. Some of these are attenuated by the contents within the container 655 and the flux that arrives at electronic sensors 685 provides an indication of the density of the contents of the container. The x-ray head 675 and the electronic sensors 685 are connected and mounted on a rotatable gantry so that the container 655 may be x-rayed from different angles.

The output from electronic sensors 685 forms the input to a Monte Carlo simulator 790 substantially similar to the one detailed in FIGS. 3 and 4. The uniformity of the output can then be filtered by filter 695 and examined by checking circuitry 696, and if the dose received in all portions of the container 655 lies between two values (determined by the particular composition of the contents, which may be stored as part of the manufacturing process control system) the x-ray head 675 gives a longer burst of x-rays 670 in order to sterilize the container 655. If the uniformity is not sufficient the control circuitry 697 may alter the angle of the x-ray head, or try a combination of different angles, and re-iterate the process to ensure that the different components in the container 655 receive a sufficient dose. If the attenuation is greatly non-uniform an alarm 698 can be sounded, and an alert message can appear on the manufacturing control system to alert an operator to the problem.

Furthermore, the various embodiments of the invention are not limited solely to Monte Carlo simulations examining deposited radiation dose. Rather, the methods and techniques described herein can also be incorporated into any type of Monte Carlo simulation examining any other type of impact, in terms of a deposition of some quantity, resulting from a multitude of directed particles travelling through a target volume. For example, the various embodiments of the invention can also be used to estimate an amount of damage in the target volume. In particular, the deposited quantity can be scored as a quantity of cell death instead of an amount of deposited radiation dose. In another example, an amount of other types of damage in the target volume can also be estimated, such as the number of broken bonds or an amount of ionization generated (i.e., deposited) by the directed particles. As one of ordinary skill in the art will recognize, a similar calculation to that used for the calculation of energy deposition or dose deposition per voxel can be used to provide an estimate of the deposition of other quantities, such as damage in each voxel. Thus, the various embodiments of the invention can be used to obtain one or more arrays, including the adjusted dose array and one or more different types of damage arrays. For example, referring to FIG. 5, step 622 can also be used to compute one or more damage arrays for use in planning radiation treatments at step 626. Therefore, a simulation in accordance with the various embodiments of the invention can be used to ascertain dose and/or estimate deposition of these other quantities, including quantities associated with damage.

Figure 7:
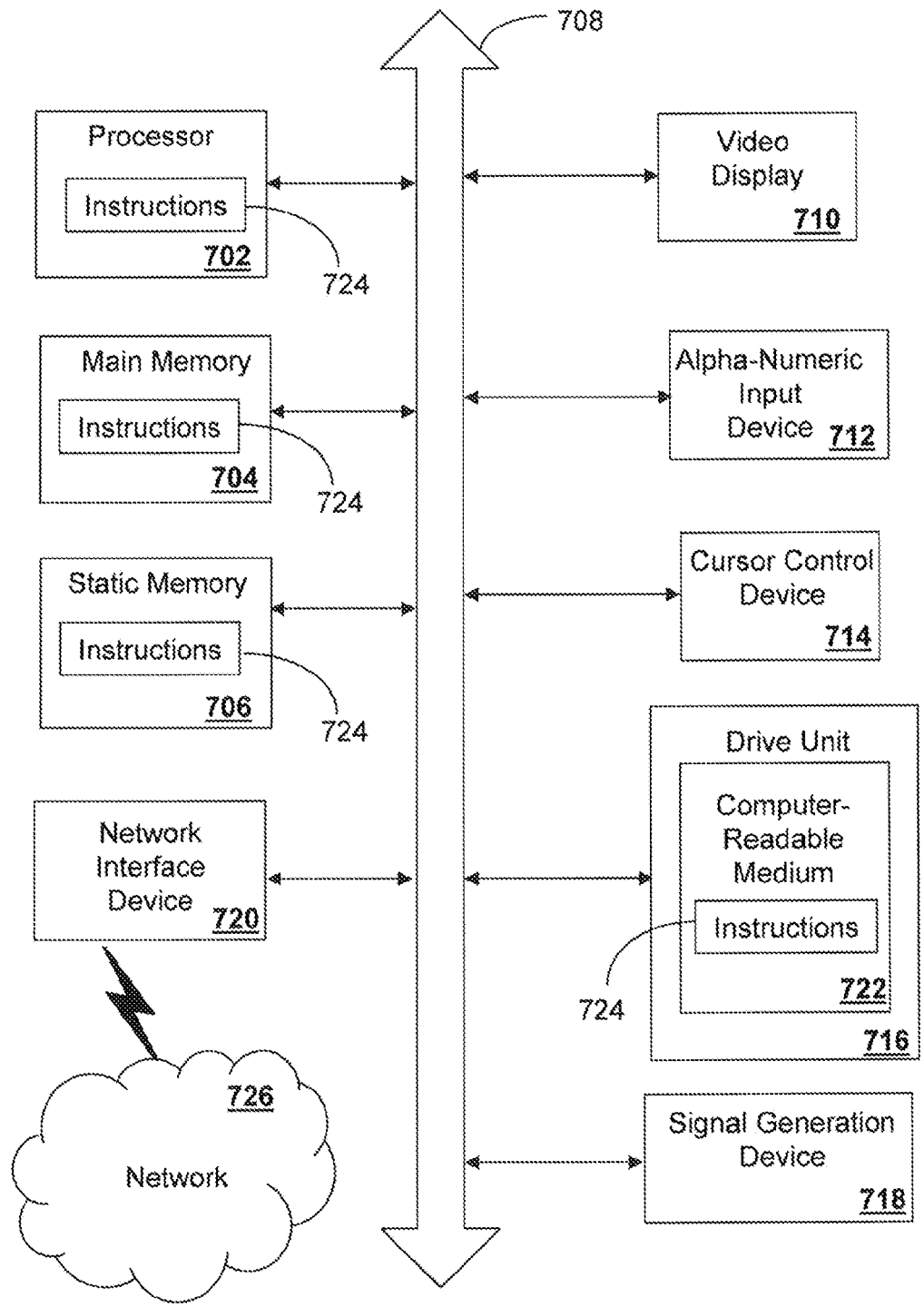
FIG. 7 is a schematic diagram of a computer system for executing a set of instructions that, when executed, can cause the computer system to perform one or more methodologies and procedures in accordance with the various embodiments of the invention.

FIG. 7 is a schematic diagram of a computer system 700 for executing a set of instructions that, when executed, can cause the computer system to perform one or more of the methodologies and procedures described above. In some embodiments of the invention, the computer system 700 operates as a standalone device. In other embodiments of the invention, the computer system 700 can be connected (e.g., using a network) to other computing devices. In a networked deployment, the computer system 700 can operate in the capacity of a server or a client developer machine in server-client developer network environment, or as a peer machine in a peer-to-peer (or distributed) network environment.

The machine can comprise various types of computing systems and devices, including a server computer, a client user computer, a personal computer (PC), a tablet PC, a laptop computer, a desktop computer, a control system, a network router, switch or bridge, or any other device capable of executing a set of instructions (sequential or otherwise) that specifies actions to be taken by that device. It is to be understood that a device of the present disclosure also includes any electronic device that provides voice, video or data communication. Further, while a single computer is illustrated, the phrase "computer system" shall be understood to include any collection of computing devices that individually or jointly execute a set (or multiple sets) of instructions to perform any one or more of the methodologies discussed herein.

The computer system 700 can include a processor 702 (such as a central processing unit (CPU), a graphics processing unit (GPU, or both), a main memory 704 and a static memory 706, which communicate with each other via a bus 708. The computer system 700 can further include a display unit 710, such as a video display (e.g., a liquid crystal display or LCD), a flat panel, a solid state display, or a cathode ray tube (CRT)). The computer system 700 can include an alpha-numeric input device 712 (e.g., a keyboard), a cursor control device 714 (e.g., a mouse), a disk drive unit 716, a signal generation device 718 (e.g., a speaker or remote control) and a network interface device 720.

The disk drive unit 716 can include a computer-readable medium 722 on which is stored one or more sets of instructions 724 (e.g., software code) configured to implement one or more of the methodologies, procedures, or functions described herein. The instructions 724 can also reside, completely or at least partially, within the main memory 704, the static memory 706, and/or within the processor 702 during execution thereof by the computer system 700. The main memory 704 and the processor 702 also can constitute machine-readable media.

Dedicated hardware implementations including, but not limited to, application-specific integrated circuits, programmable logic arrays, and other hardware devices can likewise be constructed to implement the methods described herein. Applications that can include the apparatus and systems of various embodiments of the invention broadly include a variety of electronic and computer systems. Some embodiments of the invention implement functions in two or more specific interconnected hardware modules or devices with related control and data signals communicated between and through the modules, or as portions of an application-specific integrated circuit. Thus, the exemplary system is applicable to software, firmware, and hardware implementations.

In accordance with various embodiments of the invention of the present disclosure, the methods described herein can be stored as software programs in a computer-readable medium and can be configured for running on a computer processor. Furthermore, software implementations can include, but are not limited to, distributed processing, component/object distributed processing, parallel processing, virtual machine processing, which can also be constructed to implement the methods described herein.

The present disclosure contemplates a computer-readable medium containing instructions 724 or that receives and executes instructions 724 from a propagated signal so that a device connected to a network environment 726 can send or receive voice and/or video data, and that can communicate over the network 726 using the instructions 724. The instructions 724 can further be transmitted or received over a network 726 via the network interface device 720.

While the computer-readable medium 722 is shown in an exemplary embodiment to be a single storage medium, the term "computer-readable medium" should generally be taken to include a single medium or multiple media (e.g., a centralized or distributed database, and/or associated caches and servers) that store the one or more sets of instructions. The term "computer-readable medium" shall also be taken to include any medium that is capable of storing, encoding or carrying a set of instructions for execution by the machine and that cause the machine to perform any one or more of the methodologies of the present disclosure.

The term "computer-readable medium" shall accordingly be taken to include, but not be limited to, solid-state memories such as a memory card or other package that houses one or more read-only (non-volatile) memories, random access memories, or other re-writable (volatile) memories; magneto-optical or optical medium such as a disk or tape; as well as carrier wave signals such as a signal embodying computer instructions in a transmission medium; and/or a digital file attachment to e-mail or other self-contained information archive or set of archives considered to be a distribution medium equivalent to a tangible storage medium. Accordingly, the disclosure is considered to include any one or more of a computer-readable medium or a distribution medium, as listed herein and to include recognized equivalents and successor media, in which the software implementations herein are stored.

Although the present specification describes components and functions implemented in the embodiments of the invention with reference to particular standards and protocols, the disclosure is not limited to such standards and protocols. Each of the standards for Internet and other packet switched network transmission (e.g., TCP/IP, UDP/IP, HTML, and HTTP) represent examples of the state of the art. Such standards are periodically superseded by faster or more efficient equivalents having essentially the same functions. Accordingly, replacement standards and protocols having the same functions are considered equivalents.

EXAMPLES

The following non-limiting Examples serve to illustrate selected embodiments of the invention of the invention. It will be appreciated that variations in proportions and alternatives in elements of the components shown will be apparent to those skilled in the art and are within the scope of embodiments of the invention.

Figure 8A:
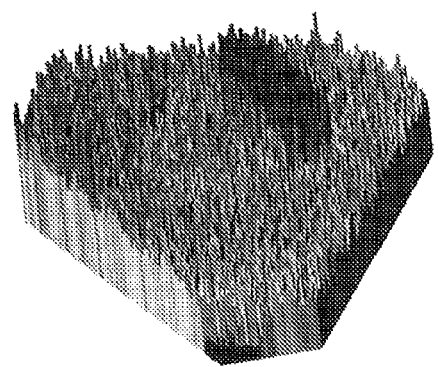
FIG. 8A shows the raw results of a Geant4 simulation of a test phantom configuration.
Figure 8B:
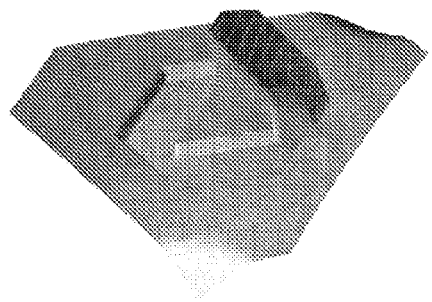
FIG. 8B shows the result of smoothing the data shown in FIG. 8A with $\sigma=5$ voxels.
Figure 8C:
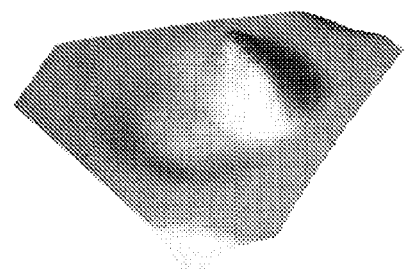
FIG. 8C shows the result of smoothing the data in FIG. 8A with $\sigma=5$ voxels and all $\mu$'s set to 1.

The first case is a radiometric test phantom comprising a set of rectangular parallelepipeds, of varying compositions, embedded in water. The compositions are roughly equivalent to human bone (ICRU44 bone composition), and to human breast tissue (BR12 plastic compositions). FIG. 8A shows the raw results of a Geant4 simulation of the test phantom. A description of the Geant 4 simulator is provided in the reference *Nuclear instruments and Methods Section A* 506 (2003), 250-303, which is hereby incorporated by reference. FIG. 8B shows the result of smoothing the data in FIG. 8A with $\sigma=5$ voxels. FIG. 8C shows the result of smoothing the data in FIG. 8A with $\sigma=5$ voxels and all $\mu$'s set to 1, i.e., classical smoothing. The phantom is 10 cm on each side, and the irradiation in the model was monochromatic 500 keV X-rays. The dose distribution was binned in a 100×100×100 grid.

Figure 8D:
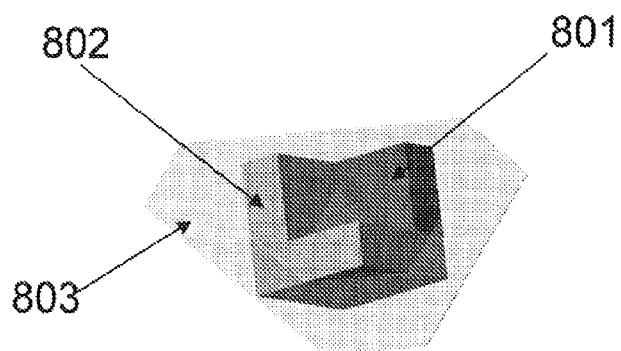
FIG. 8D shows a slice through the test phantom configuration in which dose is plotted and showing the different compositions in the test phantom.

FIG. 8D shows a slice through the test phantom in which dose is plotted and showing the different compositions in the test phantom. Areas 101 are bone, areas 102 are slightly fatty tissue, and areas 103 are water. The image in FIG. 8D is the dose on a slice through the phantom at an angle that exposes all the compositions. For the test phantom, the values of $\mu$ were varied slightly from book values of $\mu_{en}$ for the compositions therein and conditions by visually examining the behavior at composition boundaries. The $\mu$ values were also computer for this test phantom by least squares, as described below, and the values obtained were very similar. Therefore, as previously described outcome of the smoothing is not unduly sensitive to the choices in $\mu$ values. The simulation shown used $1.5 \times 10^8$ photons, for a total computing time of about 3 hours on a modern laptop computer.

A more complex, but realistic case, a beam in a model human head (head phantom) is shown with respect to FIGS. 9A-9D. In these simulations, a segmented human head data set, which has tissue types already tagged so the compositions can be easily determined, was used. For these runs, a beam of 1 MeV X-rays, in a 4 cm diameter circular beam, was simulated. Furthermore, an anisotropic smoothing kernel comprising a uniaxial Gaussian ellipsoid with s=10 mm along the direction of propagation of the beam, and s=1.5 mm transverse to the beam propagation direction was used. Such a kernel takes maximal advantage of the continuity along with beam direction, without blurring the edges of the beam too much. However, further lengthening of the smoothing along the beam can generate incorrect results in thick segments of bone, since the smoothing length is approaching the transport length. In the transverse direction, beam emittance, beam aiming, patient motion, and scatter contribute to edge width and uncertainties that are not likely to be below 1.5 mm, so no significant resolution was believed to be sacrificed by this choice. In practice, since smoothing is gained as the square of the transverse size of the kernel, the transverse width could be increased without any practical degradation of the results.

Figure 9A:
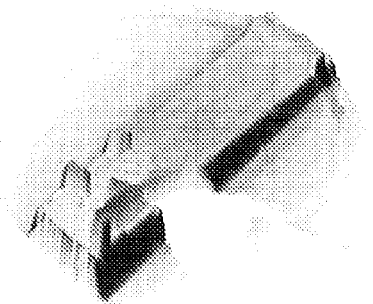
FIG. 9A shows a dose computed for a head phantom configuration in a 20 minute ($10^6$ photons) simulation according to an embodiment of the invention.
Figure 9B:
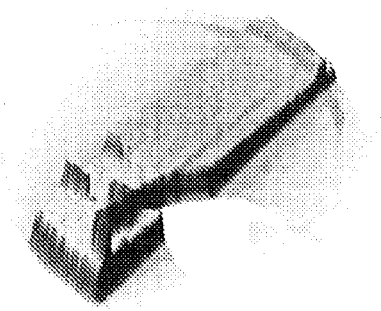
FIG. 9B shows a dose computed for a head phantom configuration in a 33 hour ($10^8$ photons) simulation according to an embodiment of the invention.
Figure 9C:
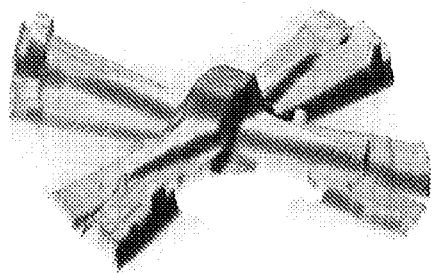
FIG. 9C shows a 4-beam 'treatment plan' computed in 16 minutes wall time. Beamlets are 2 cm diameter, with no divergence.
Figure 9D:
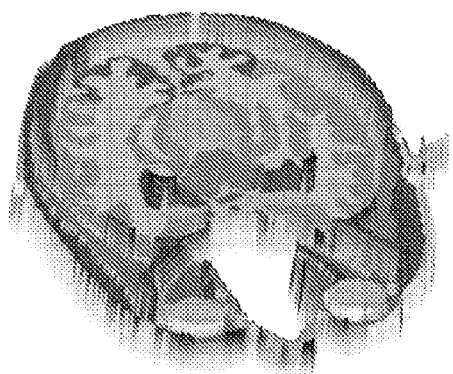
FIG. 9D shows $\mu$ values used for the head phantom configuration, displayed both as shading and height.

The results of such simulations are shown in FIG. 9A-9D. FIG. 9A shows a dose computed in a 20 minute ($10^6$ photons) simulation according to an embodiment of the invention. FIG. 9B shows a dose computed in a 33 hour ($10^8$ photons) simulation using conventional smoothing techniques. As shown by the similarities between FIGS. 9A and 9B, a similar degree of smoothing can be obtained by simulating a significantly fewer number of photons ($10^6$ versus $10^8$), resulting in the significant time reduction (20 minutes versus 33 hours) described above. FIG. 9C shows a 4-beam 'treatment plan' computed in 16 minutes wall time according to an embodiment of the invention. The term "wall time", as used herein, refers to the actual amount of time elapsed between initiating the simulation and the end of the simulation on a computer system. This is in contrast to computational or CPU time, which is the sum total of time that each of processing units of the computer system was operating while performing the simulation Beamlets are 2 cm diameter, with no divergence. FIG. 9D shows $\mu$ values used for the head phantom, displayed both as shading and height. The computation times are single-processor CPU times on a laptop computer, which demonstrates that, even without a computer cluster, these simulations can be carried out in very reasonable times on modest hardware. Since Monte Carlo computations of this type fall into the 'embarrassingly parallel' scaling class, a single processor nm can be scaled to almost any number of processors to make it faster. For real multi-beam treatment planning, it is likely that one would want to run one beamlet on each processor of a cluster to quickly build up a dose map for each beamlet, and then optimize linear combinations of the smoothed dose maps from these beamlets. Note that, when using an anisotropic kernel and multiple beamlets, the smoothing can be carried out before the beamlets are combined, since the long axis of the kernel needs to point (approximately) along the beam propagation direction.

Applicants present certain theoretical aspects above that are believed to be accurate that appear to explain observations made regarding embodiments of the invention of the invention. However, embodiments of the invention of the invention may be practiced without the theoretical aspects presented. Moreover, the theoretical aspects are presented with the understanding that Applicants do not seek to be bound by the theory presented.

While various embodiments of the invention have been described above, it should generally be understood that they have been presented by way of example only, and not limitation. Numerous changes to the disclosed embodiments of the invention can be made in accordance with the disclosure herein without departing from the spirit or scope of the invention. Thus, the breadth and scope of the invention should generally not be limited by any of the above described embodiments of the invention. Rather, the scope of the invention should generally be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments of the invention only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should generally be interpreted as having a meaning that is consistent with their meaning in the context of the relevant art and will not be interpreted in an idealized or overly formal sense unless expressly so defined herein.

What is claimed is:

1. A method for estimating a radiation dose and distribution for a target volume, the method comprising:
receiving a simulated dose array, the dose array describing a plurality of simulated dose values for a plurality of voxels in the target volume;
generating a non-uniform energy deposition coefficient function for the plurality of voxels;
obtaining a raw fluence array based at least on the simulated dose array and the energy deposition coefficient function;
generating an adjusted fluence array based on the raw fluence array and at least one adjustment function; and
generating an adjusted dose array for the target volume based on the adjusted fluence array and the energy deposition coefficient function;
wherein the adjusted dose array is of the form $$D(\bar{r}) = \mu(\bar{r})[\ldots],$$

where $\mu(\bar{r})$ is the energy deposition coefficient function which is defined by a set of coefficients which describe mean energy deposition per fluence at a specified voxel, $D(\bar{r})$ is the adjusted dose array at a specified voxel, and $\bar{r}$ is the specified voxel.

2. The method of claim 1, further comprising:
receiving a composition array describing one or more compositions associated with each of the plurality of voxels in the target volume;
wherein the generating the energy deposition coefficient function further comprises computing energy deposition coefficient values for each of the compositions in the target volume.

3. The method of claim 2, wherein:
the computing further comprises deriving the energy coefficient values such that differences in fluence values are minimized for the plurality of voxels along a border between a first of the compositions and a second of the compositions.

4. The method of claim 1, wherein:
the adjustment function comprises a smoothing function that is a weighted convolution with a kernel having an anisotropy, wherein the anisotropy is based on the direction of the flux of particles used for generating the simulated dose array.

5. The method of claim 4, wherein:
the raw fluence array has a plurality of dimensions, and the adjustment function specifies a kernel width for each of the plurality of dimensions; and
the applying the kernel function further comprises:
extending the raw fluence array in each of the dimensions by at least 1½ times the kernel width for each of the plurality of dimensions to construct a padded fluence array;
constructing a padded kernel array based on the kernel function and the dimension of the padded fluence array; and
multiplying the padded fluence array by the padded kernel array to produce values for adjusted kernel array.

6. The method of claim 5, wherein:
the multiplying comprises a fast Fourier transform multiplication of the padded fluence array and the padded kernel array.

7. The method of claim 1, wherein:
for a given voxel, the adjusted dose array is generated subsequent to the generation of the energy deposition coefficient function and the generation of adjusted fluence array, and the energy deposition coefficient function for the given voxel and the adjusted fluence array for the given voxel are used to calculate the adjusted dose array for the given voxel.

8. The method of claim 1, wherein:
the adjusted dose array is based on a product of the adjusted fluence array and the energy deposition coefficient function.

9. The method of claim 1, wherein:
the at least one adjustment function is a smoothing convolution kernel.

10. The method of claim 9, wherein:
the smoothing convolution kernel is Gaussian and is applied to voxels for which the smoothing convolution kernel is non-zero.

11. The method of claim 1, wherein:
the at least one adjustment function is an anisotropic kernel.

12. The method of claim 1, wherein:
the at least one adjustment function is an inhomogeneous kernel.

13. The method of claim 1, wherein: the at least one adjustment function comprises a number of kernels of different sizes.

14. A radiation treatment system, comprising:
a computer processing system including at least one processor and associated memory;
wherein the memory is configured to store information that represents a simulated dose array, the simulated dose array describing a plurality of simulated dose values for a plurality of voxels in a target volume comprising one or more different compositions; and
wherein the processor is configured to:
generate a non-uniform energy deposition coefficient function for the plurality of voxels as defined by the information stored in the memory;

generate a raw fluence array based at least on the simulated dose array as defined by the information stored in the memory and the energy deposition coefficient function;

generate an adjusted fluence array based on the raw fluence array and at least one adjustment function; and generate an adjusted dose array for the target volume based on the adjusted fluence array and the energy deposition coefficient function:

wherein the adjusted dose array is of the form $$D(\bar{r})=\mu(\bar{r})[\ldots],$$

where $\mu(\bar{r})$ is the energy deposition coefficient function which is defined by a set of coefficients which describe mean energy deposition per fluence at a specified voxel, $D(\underline{r})$ is the adjusted dose array at a specified voxel, and $\bar{r}$ is the specified voxel.

15. The system of claim 14, wherein:

the information stored in the memory further includes a composition array describing one or more compositions associated with each of the plurality of voxels in the target volume; and the processor is further configured during the generating of the energy deposition coefficient function to compute energy deposition coefficient values for each of the compositions in the target volume.

16. The system of claim 15, wherein:

the energy coefficient values are computed such that differences in fluence values are minimized for the plurality of voxels along a border between a first of the compositions and a second of the compositions.

17. The system of claim 14, wherein:

the adjustment function comprises a smoothing function that is a weighted convolution with a kernel having an anisotropy, wherein the anisotropy is based on the direction of the flux of particles used for generating the simulated dose array.

18. The system of claim 17, wherein:

the raw fluence array has a plurality of dimensions, and the adjustment function specifies a kernel width for each of the plurality of dimensions; and wherein the applying the kernel function further comprises:

extending the raw fluence array in each of the dimensions by at least 1½ times the kernel width for each of the plurality of dimensions to generate a padded fluence array;

constructing a padded kernel array based on the kernel function the dimension of the padded fluence array; and multiplying the padded fluence array by the padded kernel array to produce values for adjusted kernel array.

19. The system of claim 18, wherein:

the multiplying comprises a fast Fourier transform multiplication of the padded fluence array and the padded kernel array.

20. A method for estimating a radiation dose and distribution for a target volume, comprising:

receiving a simulated dose array, the dose array describing a plurality of simulated dose values for a plurality of voxels in the target volume;

generating a non-uniform energy deposition coefficient function for the plurality of voxels;

obtaining a raw fluence array based at least on the simulated dose array and the energy deposition coefficient function;

generating an adjusted fluence array based on the raw fluence array and at least one adjustment function; and generating an adjusted dose array for the target volume based on the adjusted fluence array and the energy deposition coefficient function;

wherein, for a given voxel, the adjusted dose array is generated subsequent to the generation of the energy deposition coefficient function and the generation of adjusted fluence array, and the energy deposition coefficient function for the given voxel and the adjusted fluence array for the given voxel are used to calculate the adjusted dose array for the given voxel;

wherein, the adjusted dose array for the given voxel is based on a product of the adjusted fluence array for the given voxel and the energy deposition coefficient function for the given voxel.

21. The method of claim 20, wherein:

the energy deposition coefficient function is defined by a set of coefficients that describe mean energy deposition per fluence at a specified voxel.

* * * * *